United States Patent [19]

Quenneville

[11] 4,060,654
[45] Nov. 29, 1977

[54] LAMELLAR PELLICLE FOR THERMOGRAPHY

[76] Inventor: Yves Quenneville, 2, rue d'Istanbul, Strasbourg (Bas-Rhin), France

[21] Appl. No.: 714,652

[22] Filed: Aug. 16, 1976

[51] Int. Cl.² ............................................. C09K 3/34
[52] U.S. Cl. ................................. 428/1; 128/2 H; 428/14; 428/913; 350/160 LC
[58] Field of Search ............... 428/1, 913, 14; 252/299; 360/160 LC; 23/230 LC; 128/2 H

[56] References Cited

U.S. PATENT DOCUMENTS

| | | | |
|---|---|---|---|
| 3,533,399 | 10/1970 | Goldberg | 428/1 |
| 3,661,142 | 5/1972 | Flam | 428/913 |
| 3,802,945 | 4/1974 | James | 428/1 |
| 3,847,139 | 11/1974 | Flam | 428/1 |
| 3,908,052 | 9/1975 | Sanders | 428/1 |
| 3,951,133 | 4/1976 | Reese | 428/1 |

*Primary Examiner*—Marion E. McCamish
*Attorney, Agent, or Firm*—Young & Thompson

[57] ABSTRACT

The disclosure is of a composite lamellar pellicle for producing thermographic patterns by means of liquid crystals which are spread upon an inner sheet and sandwiched between two outer sheets both of which have adequate mechanical strength for normal handling and at least one of which is transparent, all three layers preferably being poor conductors of heat and flexible without being elastic.

7 Claims, 3 Drawing Figures

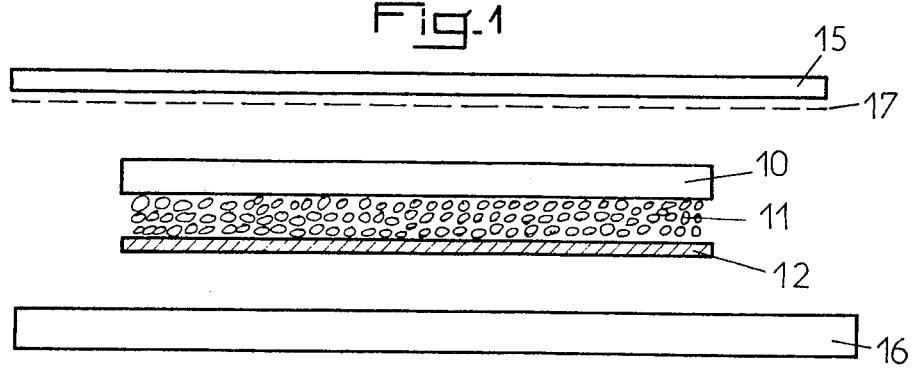
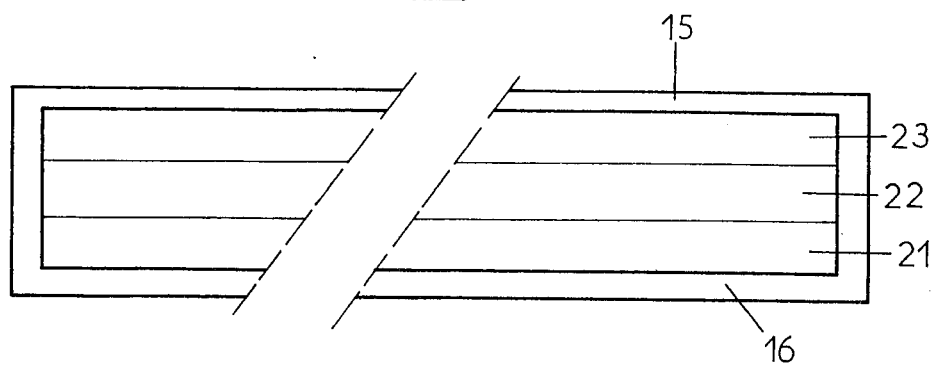
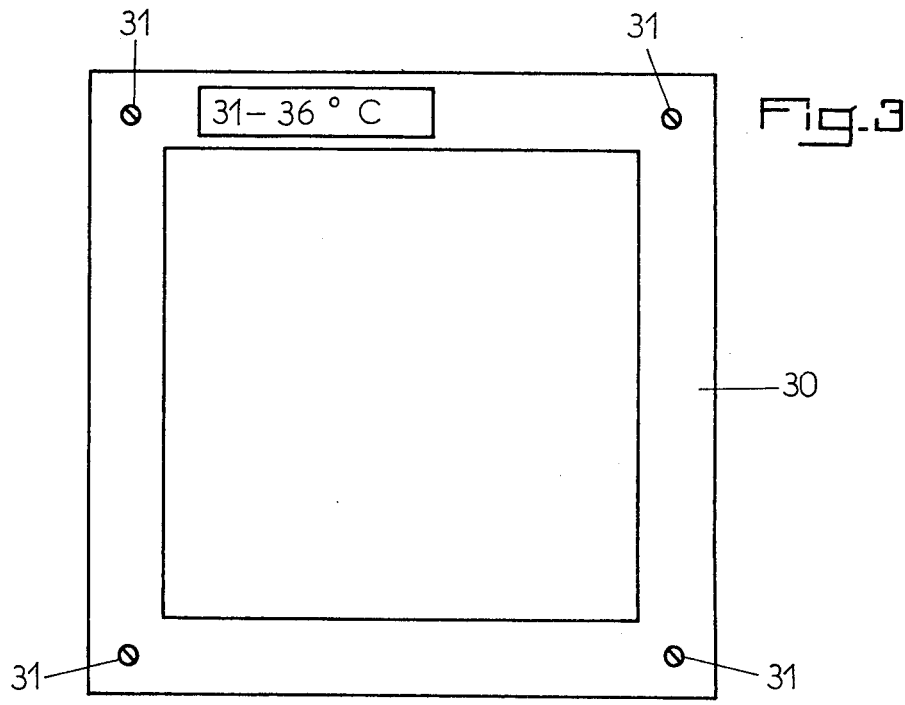

LAMELLAR PELLICLE FOR THERMOGRAPHY

INTRODUCTION AND BACKGROUND OF THE INVENTION

The present invention relates to a composite pellicle for producing thermographic representations. Such a composite pellicle serves to indicate the temperature at each point of a surface, that is to say the thermal state of this surface. The invention is concerned more particularly, but not exclusively, with the study of the distribution of the temperature at the cutaneous surface of an individual.

The representation of the distribution of the cutaneous temperatures can expose anomalies of temperature and make it possible to observe thermopathic-physiological phenomena, such as superficial veinous phenomena, and thus allows a physician to establish his diagnosis with greater certainty and rapidity. The precision and quality of such representation therefore assumes a great importance, in the degree to which an improvement in this precision makes it possible to reveal cutaneous temperature anomalies which would otherwise not be discernible. In particular, such a composite pellicle is applicable to the detection of mammary anomalies (cancer of the breast).

Thermographic representations have already been made with the use of infrared cameras, without contact between the surface being examined and the camera. Likewise thermographic representations have been made with the use of temperatureresponsive substances, mainly liquid crystals, nearly always necessitating a contact between the surface to be thermally examined and the sensor (the liquid crystals). These crystals may be deposited upon the said surface, for example like a paint, or applied through the intermediary of a flexible support disposed against the surface to be examined and conforming to this surface. There have also been utilised supports called "thermosensitive pellicles with liquid crystals".

Such pellicles are currently in use. It is known that the different parts of the pellicle take on colours which are dependent upon the temperature. Upon being applied to a surface such a pellicle assumes at each point a temperature close to that of the surface in contact, and a corresponding colouration. The representation furnished by the pellicle, which can be photographed, is a thermal image which theoretically makes it possible to know the temperature at each point. However these devices do not give complete satisfaction and are sometimes very unsatisfactory. These pellicles are fragile and easily tear or become damaged. Liquid crystals change colour only for certain respective temperatures, and it is well known that outside of a respective range of temperatures the crystals do not change colour, they are saturated and their colour gives no precise indication. Finally the diffusion of the temperature within the plane of the pellicle shows inequalities, sometimes sufficient to obscure the localised anomalies.

One object of the present invention is to provide a composite pellicle for making thermographic representations by means of thermosensitive layers of liquid crystals avoiding or mitigating the disadvantages indicated above.

BRIEF SUMMARY OF THE INVENTION

According to the invention there is utilised as a thermosensitive layer of liquid crystals a composite pellicle comprising a sheet covered with liquid crystals and furnished upon its two surfaces with thin layers of a material which is transparent and has mechanical resistance and is a very poor conductor of heat. In some instances only one of the outer layers is transparent.

FURTHER DESCRIPTIONS AND ADVANTAGES OF THE INVENTION

As the outer finishing layers are thin, the composite pellicle of the invention remains flexible, the transparency and the thinness of the outer layers ensure that the observation of the colouration of the liquid crystals is not affected, whilst the mechanical resistance or strength of the composite pellicle is greatly superior to that of a conventional pellicle. The thinness of the outer layers also has as a result not only that these layers can be as poor as possible conductors of heat but also that the composite pellicle does not unduly impede the transmission of heat in the direction perpendicular to the plane of the pellicle. The liquid crystals are thus rapidly brought to the temperature of the surface in contact with the pellicle, given that the low thermal conductivity of the layers limits the transfer of heat in the direction within the plane of the composite pellicle.

According to another feature of the invention, the composite pellicles with liquid crystals are rendered stiff in frames or bodies in order in the course of manipulations to preserve the same planar shape and thus ensure the same results during the course of various consecutive manipulations.

As the variations of colour of the liquid crystals are adequately marked within certain respective narrow ranges of temperature, according to another feature of the invention there are made thermo-responsive pellicles with liquid crystals of different kinds, selected for certain ranges of temperature, and there is constituted a collection or assembly of pellicles markes as standard, for example each for a range of 6 degrees centigrade and togther covering a wider range. Upon the frame or body of each pellicle there is placed an inscription indicative of the range of temperature whithin this pellicle gives a valid indication, preferably at a position such that it remains visible when the pellicle is located upon a medical examination pparatus. Thus the practitioner conducting the examination is precisely informed, and if a photograph is taken it is possible to read upon the photograph the range of temperatures in question.

Further features of the invention appear from the following description with reference to the accompanying drawings.

BRIEF DESCRIPTION OF THE VIEWS IN THE DRAWINGS

In the accompanying drawings

FIG. 1 is a diagrammatic and much exaggerated sectional view of the separated components of a thermographic pellicle according to the invention, FIG. 2 likewise represents a section through a second thermographic pellicle according to the invention, and FIG. 3 represents a plan of a thermographic pellicle mounted in a frame in accordance with the invention.

Detailed Description of the Preferred Embodiments

The composite pellicle of the invention, as represented by way of example in FIG. 1 comprises a transparent sheet, for example of polyester, upon one surface of which are fixed liquid crystals forming a layer 11, which is covered by an opaque layer 12 in order to absorb the incident light and improve the appearance of the colouration of the crystals.

This assembly of the sheet 10 and layers 11 and 12 is placed between two sheets 15 and 16 of polyester, which may be attached, for example by coating with transparent adhesive 17 before the assembling of the pellicle.

By way of example the sheet 10 may have a thickness of 100 microns, the layer 11 of crystals may have a thickness of 40 microns, the sheet 15 may have a thickness of 12 microns, and the sheet 16 may have a thickness of 25 microns. With advantage the sheet 15 and its adhesive are selected in such a manner as to cause the yellow colours to emerge and the least possible of the blue colours to show.

This sheet 15 and its adhesive 17 are also selected in order to ensure a good protection against ultravoilet radiation which impairs the liquid crystals. Advantageously the sheet 16 is made of matt polyester. The thermal resistance is very great within the plane of the pellicle, but is weak in the direction perpendicular to this plane. Such a pellicle is flexible without being elastic.

Such a composite pellicle may be utilised as it is, with dimensions selected for the application which is envisaged. For example, in order to reveal thermal anomalies upon the floors of dwellings (detection of heating cables) there may be selected an assembly which is a little more stiff, a little thicker, allowing the pellicle to be placed upon the floor.

It is also possible to make the pellicle adhesive in such a manner that it can be placed vertically upon a wall or a window (detection of thermal leakages). It is also possible to make the pellicle in the form of a strip or band which may be wound upon a heated conduit.

FIG. 2 represents in section a composite pellicle comprising a plurality (in this instance three) pellicles disposed edge to edge. Each pellicle is useful within a range of temperature which is easily determined. The pellicle 21 may, for example, be selected for a temperature range of 45° to 50° centigrade, the pellicle 22 for a range of 50° to 55° centigrade, and the pellicle 23 for a range of 55 ° to 60° centigrade. The assemblage also comprises a sheet 15 of material for filtering ultravoilet radiation, and a contact sheet 16. This pellicle permits exploration, with a plurality of temperature range sensitivities, without it being necessary to remove the thermosensitive pellicle, which may for example be in the form of a band or ribbon.

FIG. 3 represents in plan a body or frame 30 for fixing or stiffening a composite pellicle of the invention. This body or frame 30 may be assembled from strips or rods or from two elements connected to one another by screws 31 or rivets or the like, or by adhesive and clamping between them the margins of the composite pellicle.

The elements of the frame may be of square or rectangular shape and may be of any suitable material, for example of a moulded material, possibly such as that commercially available under the Trade Mark MAKROLON.

Preferably there is selected a material having a thermal conductivity which is close to that of the skin, in order to avoid the phenomenon of thermal effusion (sensation of cold upon touching metal or marble, for example) or warming up due to thermal insulation. Contact of the skin with an object which has a thermal conductivity greater than that of the skin, and which usually has the same temperature as the ambient atmosphere, provokes discomfort and vaso-constriction (goose pimples) that is to say disturbances in the vicinity of the surface to be examined. Thus any contact of the pellicle or frame with the skin should not cause local disturbances thereof.

Advantageously one of the sides of the frame carries an indication of the range of temperatures within which the composite pellicle can be utilised.

Such a frame is intended to be introduced into a storage or other support, arranged in such a manner as not to obscure this indication or inscription on the frame.

The composite pellicle of the invention, which is selected in a convenient manner from a series, makes it possible to reveal the thermal topography of a surface regardless of the ambient temperature, provided that the latter is compatible within the limits of utilisation of the liquid crystals and their supports, without modifying the initial thermal condition of the surface to be examined, and permits thermal comparison of two surfaces in identical conditions of utilisation, due to the arrangement in accordance with the invention.

The thermosensitive pellicle in accordance with the invention is protected against contact with the skin. In a case of sweating such contact may modify the thermal properties, and the pellicle may be moistened or cleaned with any conventional solvent.

If the phenomenon of diffusion (the colour blue of the colour corresponding to the lowest temperature) appears, two causes are possible:

a. the selected pellicle is not suitable for the existing temperature but is suitable for a range which is lower: it is necessary to select a pellicle suitable for a higher temperature range until there is observed a good thermal stability of the phenomena being studied, b. the pressure is insufficient, it is necessary to apply the pellicle a little more firmly, or to select another pellicle if the undesired phenomenon persists.

Thus due to the present invention it is possible to know whether the selected pellicle is proper in the circumstances and whether the pressure against the surface being examined is sufficient.

What is claimed is:

1. A temperature-responsive lamellar flexible pellicle for producing thermographic displays, comprising in combination a transparent inner sheet, a covering of liquid crystals which change color with temperature upon said inner sheet, an opaque inner backing sheet covering said crystals, an outer backing sheet covering said inner backing sheet, a transparent outer front sheet covering said transparent inner sheet, said outer backing sheet and said outer front sheet being of material having mechanical strength and being secured to each other by adhesive at their marginal zones, and a stiff rectangular frame in which said pellicle is mounted.

2. A pellicle as claimed in claim 1, characterised in that its external surface is transparent and is of a material which allows yellow colours to emerge with the least possible amount of the blue colours.

3. A pellicle as claimed in claim 1, characterised in that its external surface is made of a material which absorbs ultraviolet radiation.

4. A pellicle as claimed in claim 1, characterised in that the constituent material of the frame has a thermal conductivity close to that of the skin.

5. A pellicle as claimed in claim 1, in which said frame is of molded material.

6. A pellicle as claimed in claim 1, in which said frame is in two pieces secured together with said marginal zones between them.

7. A pellicle as claimed in claim 1, there being a superposed plurality of said transparent inner sheets each with a covering of liquid crystals, the liquid crystals of the various sheets being reactive to temperatures in different ranges, the pellicle being flat.

* * * * *